(12) United States Patent
Borrero

(10) Patent No.: US 12,357,545 B1
(45) Date of Patent: Jul. 15, 2025

(54) SOAP-INFUSED TOWELETTE

(71) Applicant: Dora A. Borrero, St. Petersburg, FL (US)

(72) Inventor: Dora A. Borrero, St. Petersburg, FL (US)

(*) Notice: Subject to any disclaimer, the term of this patent is extended or adjusted under 35 U.S.C. 154(b) by 432 days.

(21) Appl. No.: 18/076,477

(22) Filed: Dec. 7, 2022

Related U.S. Application Data

(60) Provisional application No. 63/328,584, filed on Apr. 7, 2022.

(51) Int. Cl.
| | | |
|---|---|---|
| *A61K 8/00* | (2006.01) | |
| *A61K 8/02* | (2006.01) | |
| *A61K 8/34* | (2006.01) | |
| *A61K 8/36* | (2006.01) | |
| *A61K 8/365* | (2006.01) | |
| *A61K 8/37* | (2006.01) | |
| *A61K 8/46* | (2006.01) | |
| *A61K 8/49* | (2006.01) | |
| *A61K 8/60* | (2006.01) | |
| *A61K 8/9783* | (2017.01) | |
| *A61Q 19/10* | (2006.01) | |
| *B65B 5/06* | (2006.01) | |
| *B65B 63/04* | (2006.01) | |

(52) U.S. Cl.
CPC ............ *A61K 8/0208* (2013.01); *A61K 8/345* (2013.01); *A61K 8/347* (2013.01); *A61K 8/361* (2013.01); *A61K 8/365* (2013.01); *A61K 8/37* (2013.01); *A61K 8/466* (2013.01); *A61K 8/4973* (2013.01); *A61K 8/602* (2013.01); *A61K 8/9783* (2017.08); *A61Q 19/10* (2013.01); *B65B 5/06* (2013.01); *B65B 63/04* (2013.01)

(58) Field of Classification Search
None
See application file for complete search history.

(56) References Cited

FOREIGN PATENT DOCUMENTS

WO    WO-9850005 A1 * 11/1998 ........... A61K 8/0212

* cited by examiner

*Primary Examiner* — Necholus Ogden, Jr.
(74) *Attorney, Agent, or Firm* — John Rizvi; John Rizvi, P.A.—The Patent Professor®

(57) ABSTRACT

The present invention provides a water-activatable soap or hand and skin cleanser composition; a water-activated single-use hand towelette; and methods for manufacture, packaging, and use. The composition comprises distilled water, aloe vera, glycerin, citric acid, butylene glycol, decyl glucoside sodium lauroyl lactylate blend, alpha olefin sulfonate, castile soap, phenoxyethanol SA, and fragrance. The composition may be infused in a towelette. The single-use hand towelette is provided in a dry state, and is moistened prior to use. The cleanser composition may be prepared by combining predetermined amounts of distilled water, aloe vera, glycerin, citric acid, and butylene glycol to provide a homogeneous "phase A" mixture; and adding and mixing, one by one, predetermined amounts of the remaining components to provide the hand and skin cleanser composition, which may have a pH of about 4.50. The towelette may be saturated with the composition, oven-dried, placed on a backing and packaged.

23 Claims, 12 Drawing Sheets

100

120
PROVIDING A DISINFECTED LABORATORY GLASS JAR 140, 144, 146

PREPARING A HOMOGENEOUS "PHASE A" SOLUTION BY:

(140, 140A-E) PROVIDING A GROUP OF "PHASE A" COMPONENTS COMPRISING: A PREDETERMINED AMOUNT OF DISTILLED WATER; A PREDETERMINED AMOUNT OF GLYCERIN; A PREDETERMINED AMOUNT OF CITRIC ACID HAVING A pH 4.50; AND A PREDETERMINED AMOUNT OF BUTYLENE GLYCOL (144) ADDING THE "PHASE A" COMPONENTS TO THE DISINFECTED LABORATORY GLASS JAR (146) STIRRING THE "PHASE A" COMPONENTS TO PROVIDE A HOMOGENEOUS "PHASE A" SOLUTION 142, 148, 152

PREPARING THE HAND AND SKIN CLEANER COMPOSITION BY:

(142, 142A-E) PROVIDING A GROUP OF "PHASE B" COMPONENTS COMPRISING: A PREDETERMINED AMOUNT OF DECYL GLUCOSIDE SODIUM LAUROYL LACTYLATE BLEND; A PREDETERMINED AMOUNT OF ALPHA OLEFIN SULFONATE; A PREDETERMINED AMOUNT OF CASTILE SOAP; A PREDETERMINED AMOUNT OF PHENOXYETHANOL SA; AND A PREDETERMINED AMOUNT OF FRAGRANCE (148) ADDING TO A REACTION MIXTURE INCLUDING THE "PHASE A" SOLUTION, THE "PHASE B" COMPONENTS, BY ADDING EACH OF THE "PHASE B" COMPONENTS TO THE REACTION MIXTURE ONE AT A TIME, WHILE MIXING THE REACTION MIXTURE UNDER GENTLE AGITATION, TO (152) PROVIDE THE HAND AND SKIN CLEANSER

150
PROVIDING A pH TESTING DEVICE AND TESTING THE HAND AND SKIN CLEANSER COMPOSITION FOR pH LEVEL, TO CONFIRM A pH OF ABOUT 4.50

> PREPARING A HOMOGENEOUS "PHASE A" SOLUTION BY:
>
> (240,240A-E) PROVIDING A GROUP OF "PHASE A" COMPONENTS COMPRISING: 18.20 OZ OF DISTILLED WATER; 1.20 OZ. OF ALOE VERA; 0.70 OZ. OF GLYCERIN; 4 TBSP. OF CITRIC ACID(pH 4.5); AND 0.50 OZ. OF BUTYLENE GLYCOL
>
> (244) ADDING THE "PHASE A" COMPONENTS TO THE DISINFECTED LABORATORY GLASS JAR
>
> (246) STIRRING THE "PHASE A" COMPONENTS TO PROVIDE A HOMOGENEOUS "PHASE A" SOLUTION 242,248,252 ⟶

> PREPARING THE HAND AND SKIN CLEANSER COMPOSITION BY:
>
> (242,242A-E) PROVIDING A GROUP OF "PHASE B" COMPONENTS COMPRISING: 1.10 OZ. OF DECYL GLUCOSIDE SODIUM LAUROYL LACTYLATE BLEND; 1.30 OZ. OF ALPHA OLEFIN SULFONATE; 1.0 OZ. OF CASTILE SOAP; 1.10 OZ. OF PHENOXYETHANOL SA; AND 100 DROPS OF FRAGRANCE
>
> (248) ADDING TO A REACTION MIXTURE INCLUDING THE "PHASE A" SOLUTION, THE "PHASE B" COMPONENTS ADDING EACH OF THE "PHASE B" COMPONENTS TO THE REACTION MIXTURE ONE AT A TIME, WHILE MIXING THE REACTION MIXTURE UNDER GENTLE AGITATION, TO(252) PROVIDE THE HAND AND SKIN CLEANSER COMPOSITION

320 ─╲
> PROVIDING A DISINFECTED LABORATORY GLASS JAR 340, 344, 346 ─╲
> PREPARING A HOMOGENEOUS "PHASE A" SOLUTION BY:
>
> (340, 340A-E) PROVIDING A GROUP OF "PHASE A" COMPONENTS COMPRISING: 18.20 OZ. OF DISTILLED WATER; 1.20 OZ. OF ALOE VERA; 0.70 OZ. OF GLYCERIN; 4 TBSP. OF CITRIC ACID (pH 4.5); AND 0.50 OZ. OF BUTYLENE GLYCOL
>
> (344) ADDING THE "PHASE A" COMPONENTS TO THE DISINFECTED LABORATORY GLASS JAR
>
> (346) STIRRING THE "PHASE A" COMPONENTS TO PROVIDE A HOMOGENEOUS "PHASE A" SOLUTION 342, 348, 352 ─╲
> PREPARING THE HAND AND SKIN CLEANSER COMPOSITION BY:
>
> (342, 342A-E) PROVIDING A GROUP OF "PHASE B" COMPONENTS COMPRISING: 1.10 OZ. OF DECYL GLUCOSIDE SODIUM LAUROYL LACTYLATE; 1.30 OZ. OF ALPHA OLEFIN SULFONATE; 01.10 OZ. OF PHENOXYETHANOL SA; AND 100 DROPS OF FRAGRANCE
>
> (348) ADDING TO A REACTION MIXTURE INCLUDING THE "PHASE A" SOLUTION, THE "PHASE B" COMPONENTS, BY ADDING EACH OF THE "PHASE B" COMPONENTS TO THE REACTION MIXTURE ONE AT A TIME, WHILE MIXING THE REACTION MIXTURE UNDER GENTLE AGITATION, TO (152) PROVIDE THE HAND AND SKIN CLEANSER COMPOSITION

350 ─╲
> PROVIDING A pH TESTING DEVICE AND TESTING THE HAND AND SKIN CLEANSER COMPOSITION FOR pH LEVEL, TO CONFIRM A pH OF ABOUT 4.50

FIG. 3

SOAP-INFUSED TOWELETTE

CROSS-REFERENCE TO RELATED APPLICATIONS

This application claims the benefit of U.S. Provisional Patent Application No. 63/328,584 filed on Apr. 7, 2022, which is incorporated by reference herein in its entirety.

FIELD OF THE INVENTION

The present invention relates generally to the field of disposable towelettes, and more particularly, to a novel soap-infused, water-activated single-use hand towelette, a water-activated soap composition, and methods for manufacture and use.

BACKGROUND OF THE INVENTION

Keeping hands clean is one of the most important steps we can take to avoid getting sick and spreading germs to others. Many diseases and conditions are spread by not washing hands with soap and clean, running water. In most cases, hand washing with soap and water is the most effective way to reduce germs on hands. Washing hands with soap and water may be preferable for a number of reasons.

Hands may become contaminated with microbes including but not limited to Hepatitis A, *Clostridium difficile*, Norovirus, *E. coli, Salmonella*, pneumonia, and the now-ubiquitous variants of Covid-19.

Waste from people or animals is a source of germs like *Salmonella, E. coli* O157, and Norovirus, which may cause diarrhea, and may cause respiratory infections like adenovirus and hand-foot-mouth disease. These kinds of germs can get onto hands after people use the toilet or change a diaper, but also in less obvious ways, like after handling raw meats that have invisible amounts of animal waste on them.

Germs may also get onto hands if people touch any object that has germs on it because someone coughed or sneezed on it or was touched by some other contaminated object. When germs get onto hands and are not washed off, they can be passed from person to person and make people sick.

Because people frequently touch their eyes, nose, and mouth without even realizing it, germs can get into the body through the eyes, nose and mouth and make us sick. Germs from unwashed hands may also get into foods and drinks while people prepare or consume them, and under certain conditions, germs can multiply in some types of foods or drinks and make people sick. Germs from unwashed hands can be transferred to other objects, like handrails, tabletops, or toys, and then transferred to another person's hands.

Removing germs through handwashing therefore helps prevent diarrhea and respiratory infections and may even help prevent skin and eye infections.

Handwashing helps people and their communities stay healthy. Handwashing education may significantly reduce the number of people who get sick with diarrhea and may reduce the incidence of respiratory illnesses, like colds. Handwashing may help reduce the incidence of variants of Covid-19. Handwashing may reduce absenteeism in schools and places of work due to gastrointestinal illness.

In addition, handwashing with soap may help combat antibiotic resistance, as preventing illness may reduce the use of antibiotics used for illnesses such as diarrhea and respiratory illnesses, and thereby lessen the likelihood that antibiotic resistance will develop. It is also important to note that handwashing can also prevent people from getting sick with germs that are already resistant to antibiotics which may be difficult to treat.

Although people around the world clean their hands with water, many people do not use soap to wash their hands. Washing hands with soap removes germs much more effectively Good handwashing early in life may even help improve child development in some settings.

In spite of the many benefits handwashing provides, handwashing is not always convenient, particularly where plumbing is not available. In some locations, in spite of plumbing being available, soap is often not provided. In such situations, many individuals may fail to maintain sufficient hand hygiene. A suitable solution is needed.

No alternatives exist which are as effective and healthy as soap-based hand cleansers. Moist towelettes are available for use to remove makeup, hand sanitizing towelettes are commercially available, and antibacterial surface cleaning wipes are available for cleaning surfaces. However, no effective options exist for hand washing and hand cleaning with soap.

While hand sanitizing compositions and sanitizing wipes exist, hand washing remains the most preferred way to clean hands. In most cases, hand washing with soap and water is the most effective way to reduce germs on hands. Washing hands with soap and water may be preferable for a number of reasons not limited to those discussed herein.

Though hand sanitizers provide a temporary remedy and are easily obtained, hand sanitizers are inconvenient, and are ultimately damaging and unhealthy. Carrying a bottle of hand sanitizer may be impractical. In addition, hand sanitizer has a negative effect on the health of the skin and may pose other health problems. Hand sanitizer is abrasive and irritating to the skin, and may cause skin dryness and damage, and cracked skin (allowing bacteria to infiltrate). Hand sanitizer may also cause alcohol poisoning, ocular irritation, and contact dermatitis.

Ideally, it would be extremely useful to provide a convenient way to clean hands with soap, in settings and situations in which soap is not provided or is unavailable. For example, there remains an unresolved need for a cleansing wipe system which provides a clean, convenient way of cleaning hands. There also remains a need for a portable option available for those traveling or on the go.

Accordingly, there is need for a solution to at least one of the aforementioned problems. For instance, there is an established need for a soap-infused, water-activated single-use hand towelette, a water-activated soap composition, and methods for manufacture.

SUMMARY OF THE INVENTION

In view of the foregoing problems in the known consumer soap and towelette fields, and lack of consumer options, the present invention provides a novel soap-infused, water-activated single-use hand towelette, a water-activated soap composition, and methods for manufacture and use.

In one aspect, the present invention provides a soap-infused water-activatable single-use hand towelette which is provided in a dry form, and is further capable of use as a dry towelette.

In one aspect, the present invention provides an efficient and effective method for making a soap-infused, water-activated single-use hand towelette.

In one aspect, the present invention provides a water-activated soap composition capable of being impregnated into a single-use hand towelette.

In one aspect, the present invention provides a method for using a water-activatable single-use hand towelette. The single-use hand towelette is provided in a dry state, and is moistened prior to use.

In a first implementation, the present invention may provide a soap or hand cleansing composition comprising one or more of the following components and combinations thereof: distilled water, aloe vera, glycerin, citric acid, butylene glycol, a blend of decyl glucoside sodium lauroyl lactylate, alpha olefin sulfonate, castile soap, phenoxyethanol SA, and fragrance. The fragrance may be any suitable fragrance or fragrance composition. The composition may be infused in a towelette comprising a nonwoven fabric.

In one aspect, the present invention may provide a soap or hand cleansing composition comprising:
  distilled water;
  aloe vera;
  glycerin;
  citric acid;
  butylene glycol;
  decyl glucoside sodium lauroyl lactylate;
  alpha olefin sulfonate;
  castile soap;
  phenoxyethanol SA; and
  fragrance.

In one aspect, the present invention may provide a soap or hand cleansing composition comprising the following components:
  18.2 oz. of distilled water;
  1.20 oz. of aloe vera;
  0.70 oz. of glycerin;
  4 tbsp. of citric acid (pH 4.5);
  0.50 oz. of butylene glycol;
  1.10 oz. of decyl glucoside sodium lauroyl lactylate blend;
  1.30 oz. of alpha olefin sulfonate;
  1.0 oz of castile soap;
  1.10 oz. of a phenoxyethanol SA; and
  100 drops of fragrance.

In another aspect, the composition may comprise these components in an equivalent proportion but in larger quantities. In yet another aspect, the composition may comprise these components in an equivalent proportion but in smaller quantities.

In a second implementation, the present invention provides a method for preparing a hand and skin cleanser composition, comprising one or more of the following steps and combinations thereof:
  providing a disinfected laboratory glass jar;
  providing a group of "phase A" components comprising:
    a predetermined amount of distilled water;
    a predetermined amount of aloe vera;
    a predetermined amount of glycerin;
    a predetermined amount of citric acid having a pH 4.50; and
    a predetermined amount of butylene glycol;
  providing a group of "phase B" components comprising:
    a predetermined amount of decyl glucoside sodium lauroyl lactylate;
    a predetermined amount of alpha olefin sulfonate;
    a predetermined amount of castile soap;
    a predetermined amount of phenoxyethanol SA; and
    a predetermined amount of fragrance;
  adding the "phase A" components to the disinfected laboratory glass jar;
  stirring the "phase A" components to provide a homogeneous "phase A" solution;
  adding to a reaction mixture including the "phase A" solution, the "phase B" components, adding each of the "phase B" components to the reaction mixture one at a time, while mixing the reaction mixture under gentle agitation, to provide the hand and skin cleanser composition; and
  providing a pH testing device and testing the hand and skin cleanser composition for pH level, to confirm a pH of about 4.50.

In one aspect, the method may include:
  providing a group of "phase A" components comprising:
    18.2 oz. of distilled water;
    1.20 oz. of aloe vera;
    0.70 oz. of glycerin;
    4 tbsp. of citric acid (pH 4.5); and
    0.50 oz. of butylene glycol; and
  providing a group of "phase B" components comprising:
    1.10 oz. of decyl glucoside sodium lauroyl lactylate blend;
    1.30 oz. of alpha olefin sulfonate;
    1.0 oz of castile soap;
    1.10 oz. of a phenoxyethanol SA; and
    100 drops of fragrance.

In one aspect, the present invention provides a method for preparing a hand and skin cleanser composition, comprising:
  providing a disinfected laboratory glass jar;
  providing a group of "phase A" components comprising:
    18.2 oz. of distilled water;
    1.20 oz. of aloe vera;
    0.70 oz. of glycerin;
    4 tbsp. of citric acid (pH 4.5); and
    0.50 oz. of butylene glycol;
  providing a group of "phase B" components comprising:
    1.10 oz. of decyl glucoside sodium lauroyl lactylate blend;
    1.30 oz. of alpha olefin sulfonate;
    1.0 oz of castile soap;
    1.10 oz. of a phenoxyethanol SA; and
    100 drops of fragrance;
  adding the "phase A" components to the disinfected laboratory glass jar;
  stirring the "phase A" components to provide a homogeneous "phase A" solution;
  adding to a reaction mixture including the "phase A" solution, the "phase B" components, adding each of the "phase B" components to the reaction mixture one at a time, while mixing the reaction mixture under gentle agitation, to provide the hand and skin cleanser composition; and
  providing a pH testing device and testing the hand and skin cleanser composition for pH level, to confirm a pH of about 4.50.

In a third implementation of the invention, a method for making or manufacturing a soap-infused, water activated single-use hand towelette is provided. The method for making the towelette may comprise the steps of preparing a water-activatable soap composition; and infusing the water-activatable soap composition in a suitable single-use hand towelette.

In one aspect, preparing the water-activatable soap composition comprises mixing a hand and skin cleanser composition as described herein.

In one aspect, the step of impregnating a cloth with the cleaning composition comprises providing a suitable cloth, immersing the cloth in the cleaning composition, saturating the cloth with the cleaning composition to impregnate the cloth with the cleaning composition, and thoroughly drying the cloth that has been saturated with cleaning composition in an oven, thereby impregnating the cleaning composition into the cloth.

In one aspect, the present invention provides a method for manufacturing a towelette infused with a hand and skin cleanser, comprising the following steps:
  providing a square or rectangular glassware dish;
  providing at least one towelette made of a nonwoven fabric; providing at least one stackable backing sheet; providing an oven safe cooking sheet; providing an oven; providing a predetermined quantity of a hand and skin cleanser composition as described herein;
  placing the at least one towelette in the glassware dish;
  adding the predetermined quantity of the hand and skin cleanser to the glassware dish;
  permitting the at least one towelette to become saturated with hand and skin cleanser in the glassware dish;
  removing the at least one towelette from the glassware dish;
  placing the at least one towelette on the at least one stackable backing sheet, to form a backed towelette;
  placing the at least one backed towelette on the oven safe cooking sheet;
  preheating the oven to a temperature of between about 180 degrees F. to about 200 degrees F.;
  placing the cooking sheet with the at least one backed towelette thereon, into the preheated oven;
  baking the at least one backed towelette for about 20 minutes;
  removing the cooking sheet with the at least one backed towelette thereon, from the oven; and
  permitting the at least one backed towelette to cool for about 30 minutes.

In a fourth implementation, the present invention may provide a packaging method comprising providing a container, providing a plurality of single-use hand towelettes as described herein, and packaging the plurality of single-use hand towelettes in a portable package.

In one aspect, the present invention provides a method for packaging at least one towelette infused with a hand and skin cleanser, comprising the following steps:
  providing at least one backed towelette infused with hand and skin cleanser as disclosed herein;
  providing a container package configured to hold the at least one backed towelette, the container package comprising a container body and a recloseable container cover or lid;
  folding the at least one backed towelette in half;
  placing the at least one backed towelette in the container body of the container package; and
  closing the container cover or lid.

In one aspect, the present invention may provide a method for manufacture of a single-use hand towelette infused with a water-activatable hand and skin cleanser, comprising one or more of the following steps and combinations thereof:
  providing a disinfected laboratory glass jar; providing a square or rectangular glassware dish;
  providing at least one towelette of a nonwoven fabric;
  providing at least one stackable backing sheet; providing an oven safe cooking sheet;
  providing an oven;
  providing a group of "phase A" components comprising:
    18.2 oz. of distilled water;
    1.20 oz. of aloe vera;
    0.70 oz. of glycerin;
    4 tbsp. of citric acid (pH 4.5); and
    0.50 oz. of butylene glycol;
  providing a group of "phase B" components comprising:
    1.10 oz. of decyl glucoside sodium lauroyl lactylate blend;
    1.30 oz. of alpha olefin sulfonate;
    1.0 oz of castile soap;
    1.10 oz. of a phenoxyethanol SA; and
    100 drops of fragrance;
  adding the "phase A" components to the disinfected laboratory glass jar;
  stirring the "phase A" components to provide a homogeneous "phase A" solution;
  adding to a reaction mixture including the "phase A" solution, the "phase B" components, adding each of the "phase B" components to the reaction mixture one at a time, while mixing the reaction mixture under gentle agitation, to provide the hand and skin cleanser composition;
  providing a pH testing device and testing the hand and skin cleanser composition for pH level, to confirm a pH of about 4.50;
  providing a predetermined quantity of the hand and skin cleanser composition as described herein;
  placing the at least one towelette in the glassware dish;
  adding the predetermined quantity of the hand and skin cleanser composition to the glassware dish;
  permitting the at least one towelette to become saturated with hand and skin cleanser composition in the glassware dish;
  removing the at least one towelette from the glassware dish;
  placing the at least one towelette on the at least one stackable backing sheet, to form a backed towelette;
  placing the at least one backed towelette on the oven safe cooking sheet;
  preheating the oven to a temperature of between about 180 degrees F. to about 200 degrees F.;
  placing the cooking sheet with the at least one backed towelette thereon, into the preheated oven;
  baking the at least one backed towelette for about 20 minutes;
  removing the cooking sheet with the at least one backed towelette thereon, from the oven;
  permitting the at least one backed towelette to cool for about 30 minutes;
  providing a container package configured to hold the at least one backed towelette, the container package comprising a container body and a recloseable container cover or lid;
  folding the at least one backed towelette in half;
  placing the at least one backed towelette in the container body of the container package; and
  sealing the container package or closing the container cover or lid.

In one aspect, the container package may be configured to enclose a single backed towelette that is individually wrapped.

In one aspect, the container package may be configured to enclose a plurality of individually wrapped towelettes.

In one aspect, the container package may be configured to enclose a plurality of backed towelettes that are stacked therein.

In one aspect, the container package may enclose 24 towelettes.

In a fifth implementation, the present invention provides a method for use of a towelette infused with a hand and skin cleanser, comprising the following steps:

providing a container package enclosing at least one backed towelette infused with a hand and skin cleanser as described herein;

removing a backed towelette infused with a hand and skin cleanser from the container package;

removing a towelette infused with a hand and skin cleanser from the backed towelette;

activating the hand and skin cleanser infused in the towelette by adding water to the towelette;

cleaning a user's hands by wiping the user's hands with the towelette; and disposing the towelette after use.

The soap infused towelette of the present invention resolves a long felt and unresolved need for effective portable soap-based hand cleaning while traveling or on the go, or for use in locations where soap is unavailable. The soap infused hand towelette solves the ongoing problem of keeping hands clean, that has become a more urgent problem during the Covid-19 pandemic or flu season. The present invention helps users keep their hands clean and healthy anywhere, anytime by just adding water to a towelette to lather the soap to properly wash hands. The towelette may be beneficially used on the go, so users no longer need to depend on the availability of soap or a soap dispenser to properly wash their hands.

During the Covid-19 pandemic, in which it is necessary to wash hands frequently to keep them clean, the soap infused towelette of the present invention makes it possible to keep hands clean on the go, by simply adding water to the towelette for use. The hand soap infused towelette remedies stress that may be caused in situations where no soap is available, and releases the user from dependency on others to provide soap in public accommodations so users may wash their hands appropriately at any establishment, business, restaurant, park, camping area, boating area, the beach, or the like.

The hand towelette of the present invention differs from and distinguishes over previous solutions which ignore the effectiveness of soap and water in removing germs, dirt, microbes (bacteria, viruses) and chemicals on the hands.

The present invention provides an unprecedented superior solution to hand sanitizers and other available options. As compared to conventional hand sanitizers, when using the present invention there is no need to carry a bottle of hand sanitizer or soap. The light weight (or weightless) towelette of the present invention is already infused with soap. In addition, the present invention avoids exposure to the negative effect on the health of the skin and other health problems caused by hand sanitizers as described herein. The soap infused hand towelette of the present invention may be used to gently clean hands. The present invention provides a safe and gentle way to promote and maintain clean, healthy hands. The present invention also brings reassurance to families that they may maintain the cleanliness of their hands in any situation or setting, and do so with a product that offers quality and special ingredients which keep hands clean and healthy, while contributing to the overall health of the families.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 1 presents a flow chart of a method in accordance with an exemplary embodiment of the present invention;

FIG. 2 presents a flow chart of a method in accordance with an exemplary embodiment of the present invention;

FIG. 3 presents a flow chart of a method in accordance with an exemplary embodiment of the present invention;

Like reference numerals refer to like parts throughout the several views of the drawings.

DETAILED DESCRIPTION

Figure 4:
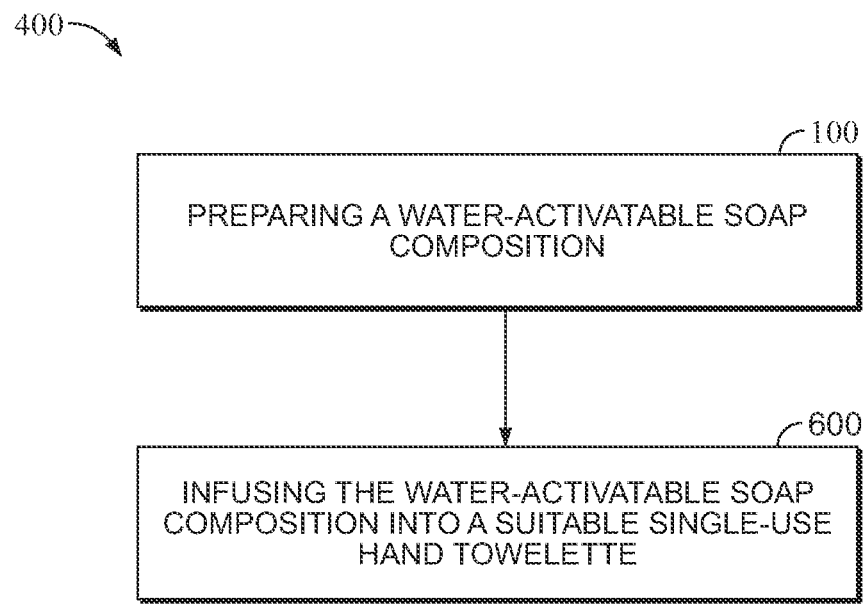
FIG. 4 presents a flow chart of a method in accordance with an exemplary embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed to a novel water-activatable soap composition, a soap-infused, water-activated single-use hand towelette, a package container enclosing at least one single-use towelette, and methods for formulating, manufacture, packaging, and use.

In an exemplary embodiment, the present invention provides a soap or hand cleansing composition comprising one or more of the following components and combinations thereof: distilled water, aloe vera, glycerin, citric acid, butylene glycol, decyl glucoside sodium lauroyl lactylate, alpha olefin sulfonate, castile soap; phenoxyethanol SA, and fragrance. The composition may be infused in a towelette comprising a nonwoven fabric.

In some embodiments, the present invention may provide a soap or hand cleansing composition comprising:
- a predetermined amount of distilled water;
- a predetermined amount of aloe vera;
- a predetermined amount of glycerin;
- a predetermined amount of citric acid (pH 4.5);
- a predetermined amount of butylene glycol;
- a predetermined amount of decyl glucoside sodium lauroyl lactylate;
- a predetermined amount of alpha olefin sulfonate;
- a predetermined amount of castile soap;
- a predetermined amount of phenoxyethanol SA; and
- a predetermined amount of at least one fragrance.

In some embodiments, the present invention may provide a soap or hand cleansing composition comprising:
- 18.2 oz. of distilled water;
- 1.20 oz. of aloe vera;
- 0.70 oz. of glycerin;
- 4 tbsp. of citric acid (pH 4.5);
- 0.50 oz. of butylene glycol;
- 1.10 oz. of decyl glucoside sodium lauroyl lactylate blend;
- 1.30 oz. of alpha olefin sulfonate;
- 1.0 oz of castile soap;
- 1.10 oz. of a phenoxyethanol SA; and
- 100 drops of fragrance.

The components may come from any suitable commercial source. The fragrance may be any suitable fragrance including at least one fragrance or a fragrance blend.

The present invention may provide an efficient and effective method for making a water-activatable soap composition capable of being impregnated into a single-use hand towelette.

Referring now to FIG. 1, in an exemplary embodiment, the present invention provides a method 100 for preparing a hand and skin cleanser composition, comprising one or more of the following steps and combinations thereof:
- 120 providing a disinfected laboratory glass jar;
- 140 providing a group of "phase A" components comprising:
  - 140A a predetermined amount of distilled water;
  - 140B a predetermined amount of aloe vera;
  - 140C a predetermined amount of glycerin;
  - 140D a predetermined amount of citric acid having a pH 4.50; and
  - 140E a predetermined amount of butylene glycol;
- 142 providing a group of "phase B" components comprising:
  - 142A a predetermined amount of decyl glucoside sodium lauroyl lactylate blend;
  - 142B a predetermined amount of alpha olefin sulfonate;
  - 142C a predetermined amount of castile soap;
  - 142D a predetermined amount of a phenoxyethanol SA; and
  - 142E a predetermined amount of fragrance;
- 144 adding the "phase A" components to the disinfected laboratory glass jar;
- 146 stirring the "phase A" components to provide a homogeneous "phase A" solution;
- 148 adding to a reaction mixture including the "phase A" solution, the "phase B" components, adding each of the "phase B" components to the reaction mixture one at a time, while mixing the reaction mixture under gentle agitation, to 152 provide the hand and skin cleanser composition; and
- 150 providing a pH testing device and testing the hand and skin cleanser composition for pH level, to confirm a pH of about 4.50.

As shown at FIG. 2, in some embodiments, in preparation of the homogeneous "Phase A" solution, the step of providing a group of "phase A" components 240 may further comprise providing:
- 240A 18.20 oz. of distilled water; 240B 1.20 oz. of aloe vera;
- 240C 0.70 oz. of glycerin;
- 240D 4 tbsp. of citric acid (pH 4.5); and
- 240E 0.50 oz. of butylene glycol.

As also shown at FIG. 2, the step of providing a group of "Phase B" components 242 may further comprise providing:
- 242A 1.10 oz. of decyl glucoside sodium lauroyl lactylate blend;
- 242B 1.30 oz. of alpha olefin sulfonate;
- 242C 1.0 oz of castile soap;
- 242D 1.10 oz. of a phenoxyethanol SA; and
- 242E 100 drops of fragrance.

In some embodiments, as shown at FIG. 3, the method 300 for preparing a hand and skin cleanser composition, may comprise one or more of the following steps and combinations thereof:
- 320 Providing a disinfected laboratory glass jar;
- 340 Providing a group of "phase A" components comprising:
  - 340A 18.2 oz. of distilled water;
  - 340B 1.20 oz. of aloe vera;
  - 340C 0.70 oz. of glycerin;
  - 340D 4 tbsp. of citric acid (pH 4.5); and
  - 340E 0.50 oz. of butylene glycol;
- 342 providing a group of "phase B" components comprising:
  - 342A 1.10 oz. of decyl glucoside sodium lauroyl lactylate blend;
  - 342B 1.30 oz. of alpha olefin sulfonate;
  - 342C 1.0 oz. of castile soap;
  - 342D 1.10 oz. of a phenoxyethanol SA; and
  - 342E 100 drops of fragrance;
- 344 adding the "phase A" components to the disinfected laboratory glass jar;
- 346 stirring the "phase A" components to provide a homogeneous "phase A" solution;
- 348 adding to a reaction mixture including the "phase A" solution, the "phase B" components, adding each of the "phase B" components to the reaction mixture one at a time, while mixing the reaction mixture under gentle agitation, to 352 provide the hand and skin cleanser composition; and
- 350 providing a pH testing device and testing the hand and skin cleanser composition for pH level, to confirm a pH of about 4.50.

In an exemplary embodiment, as shown at FIG. 4, the present invention may provide a method 300 for making or manufacturing a soap-infused, water activated single-use hand towelette. The method for making the towelette may comprise the steps of preparing a water-activatable soap composition 100; and infusing the water-activatable soap composition in a suitable single-use hand towelette 600.

In some embodiments, preparing the water-activatable soap composition comprises mixing a hand and skin cleanser composition as described herein.

Figure 5:
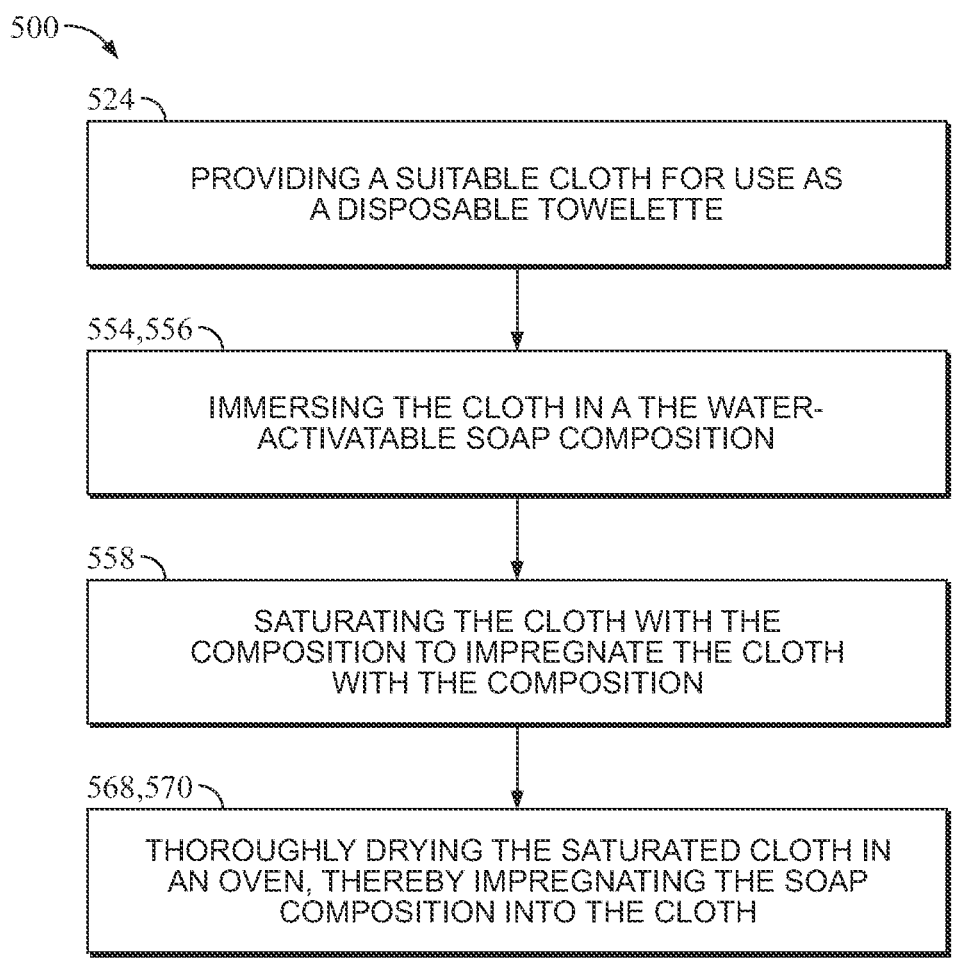
FIG. 5 presents a flow chart of a method in accordance with an exemplary embodiment of the present invention.

As seen at FIG. 5, in some embodiments, infusing the water-activatable soap composition may comprise impregnating a cloth with the cleaning composition by providing a suitable cloth 524, immersing the cloth in the cleaning composition 554, 556 saturating the cloth with the cleaning composition to impregnate the cloth with the cleaning composition 558, and thoroughly drying the cloth that has been saturated with cleaning composition in an oven 568, thereby impregnating the cleaning composition into the cloth 570.

Figure 6:
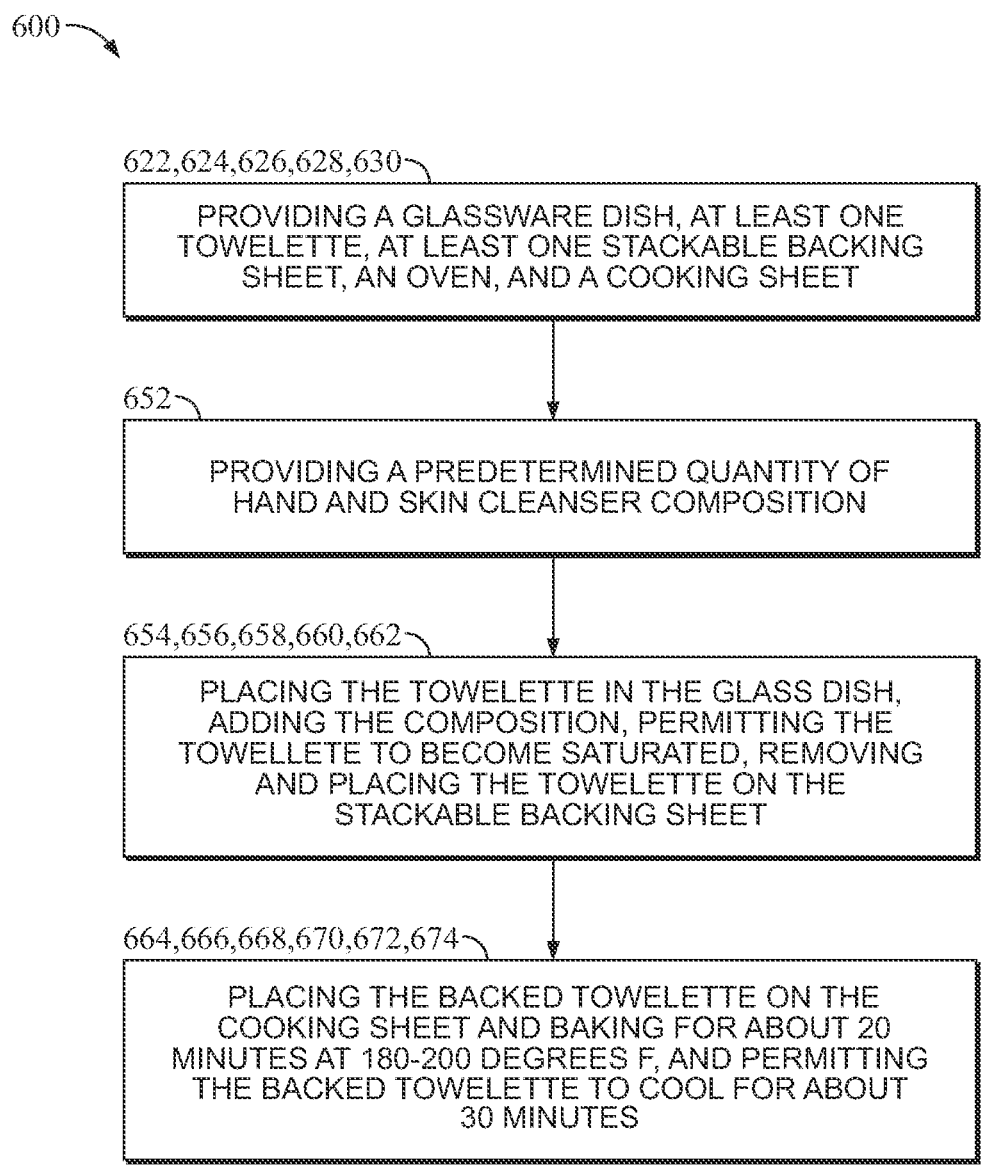
FIG. 6 presents a flow chart of a method in accordance with an exemplary embodiment of the present invention.

Referring to FIG. 6, in some embodiments, the present invention provides a method 600 for manufacturing a towelette infused with a hand and skin cleanser, comprising the following steps:
- 622 providing a square or rectangular glassware dish;
- 624 providing at least one towelette made of a nonwoven fabric;
- 626 providing at least one stackable backing sheet;
- 628 providing an oven;
- 630 providing an oven safe cooking sheet;
- 652 providing a predetermined quantity of a hand and skin cleanser composition as described herein;
- 654 placing the at least one towelette in the glassware dish;
- 656 adding the predetermined quantity of the hand and skin cleanser to the glassware dish;
- 658 permitting the at least one towelette to become saturated with hand and skin cleanser in the glassware dish;
- 660 removing the at least one towelette from the glassware dish;
- 662 placing the at least one towelette on the at least one stackable backing sheet, to form a backed towelette;
- 664 placing the at least one backed towelette on the oven safe cooking sheet;
- 666 prebeating the oven to a temperature of between about 180 degrees F. to about 200 degrees F.;
- 668 placing the cooking sheet with the at least one backed towelette thereon, into the preheated oven;
- 670 baking the at least one backed towelette for about 20 minutes;
- 672 removing the cooking sheet with the at least one backed towelette thereon, from the oven; and
- 674 permitting the at least one backed towelette to cool for about 30 minutes;
- 676 thereby providing at least one backed towelette infused with a hand and skin cleanser.

Figure 7:
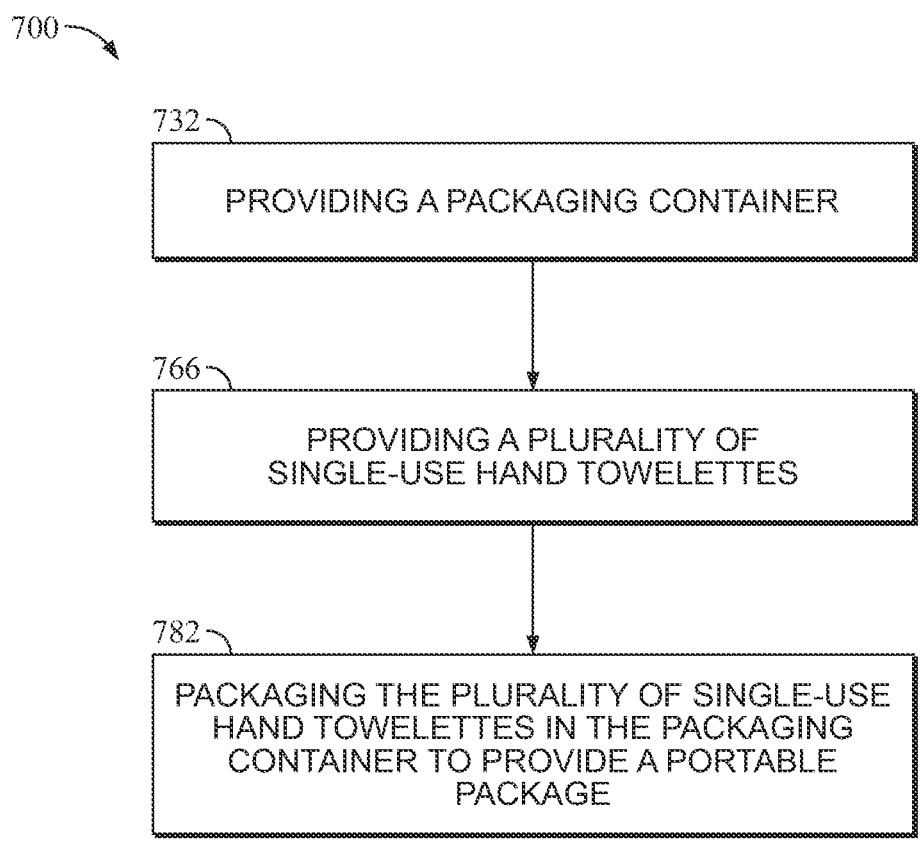
FIG. 7 presents a flow chart of a method in accordance with an exemplary embodiment of the present invention.

As shown at FIG. 7, in an exemplary embodiment, the present invention may provide a packaging method 700 comprising providing a packaging container 732, providing a plurality of single-use hand towelettes as described herein 766, and packaging the plurality of single-use hand towelettes in a portable package 782.

Figure 8:
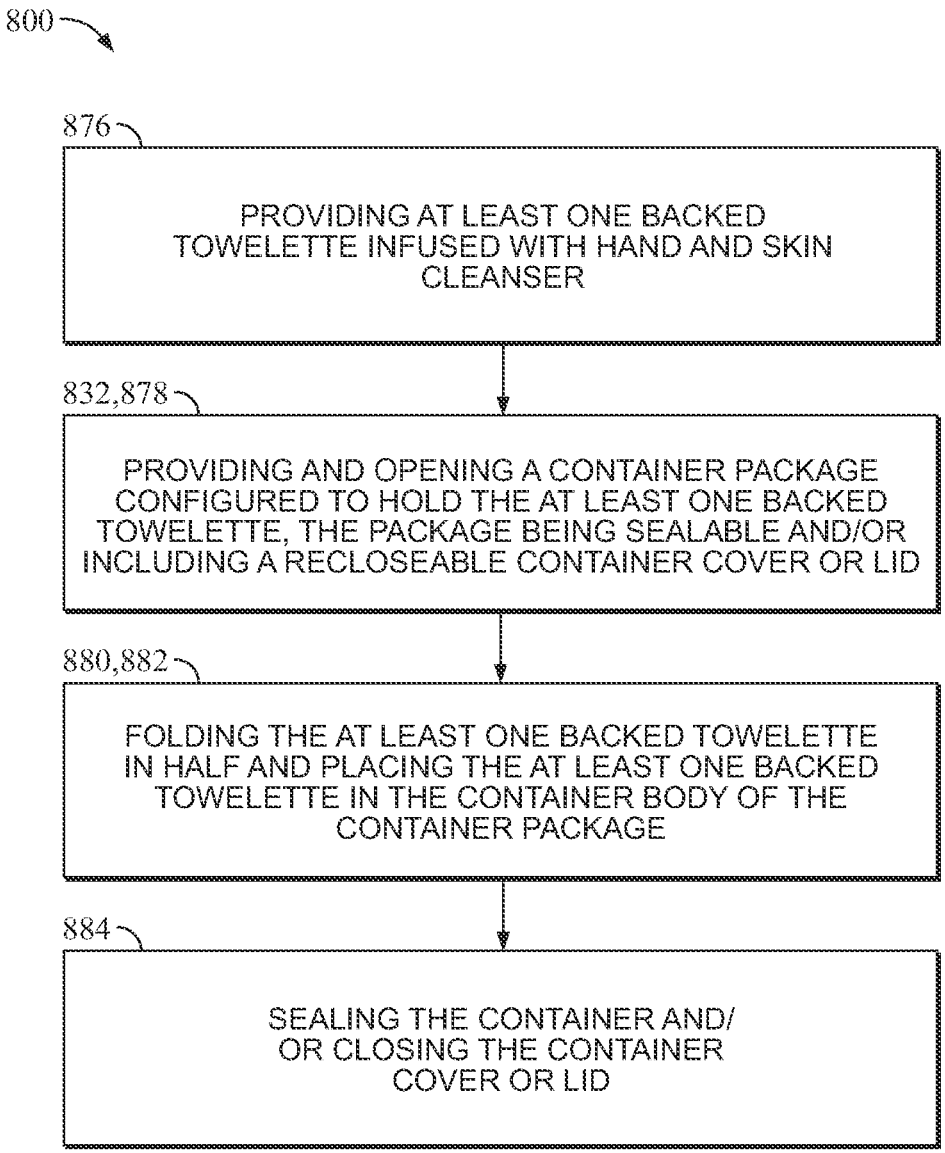
FIG. 8 presents a flow chart of a method in accordance with an exemplary embodiment of the present invention.

As shown at FIG. 8, the present invention may provide a method 800 for packaging at least one towelette infused with a hand and skin cleanser, comprising the following steps:
- 876 providing at least one towelette infused with hand and skin cleanser as disclosed herein;
- 832, 878 providing and opening a container package configured to hold the at least one towelette, the container package comprising a container body and being resealable or including a recloseable container cover or lid;
- 880 folding the at least one towelette in half;
- 882 placing the at least one towelette in the container body of the container package; and 884 sealing or closing the container cover or lid sealing the container package or closing the container cover or lid, to provide at least one single-use towelette infused with a hand and skin cleanser composition.

Figure 9:
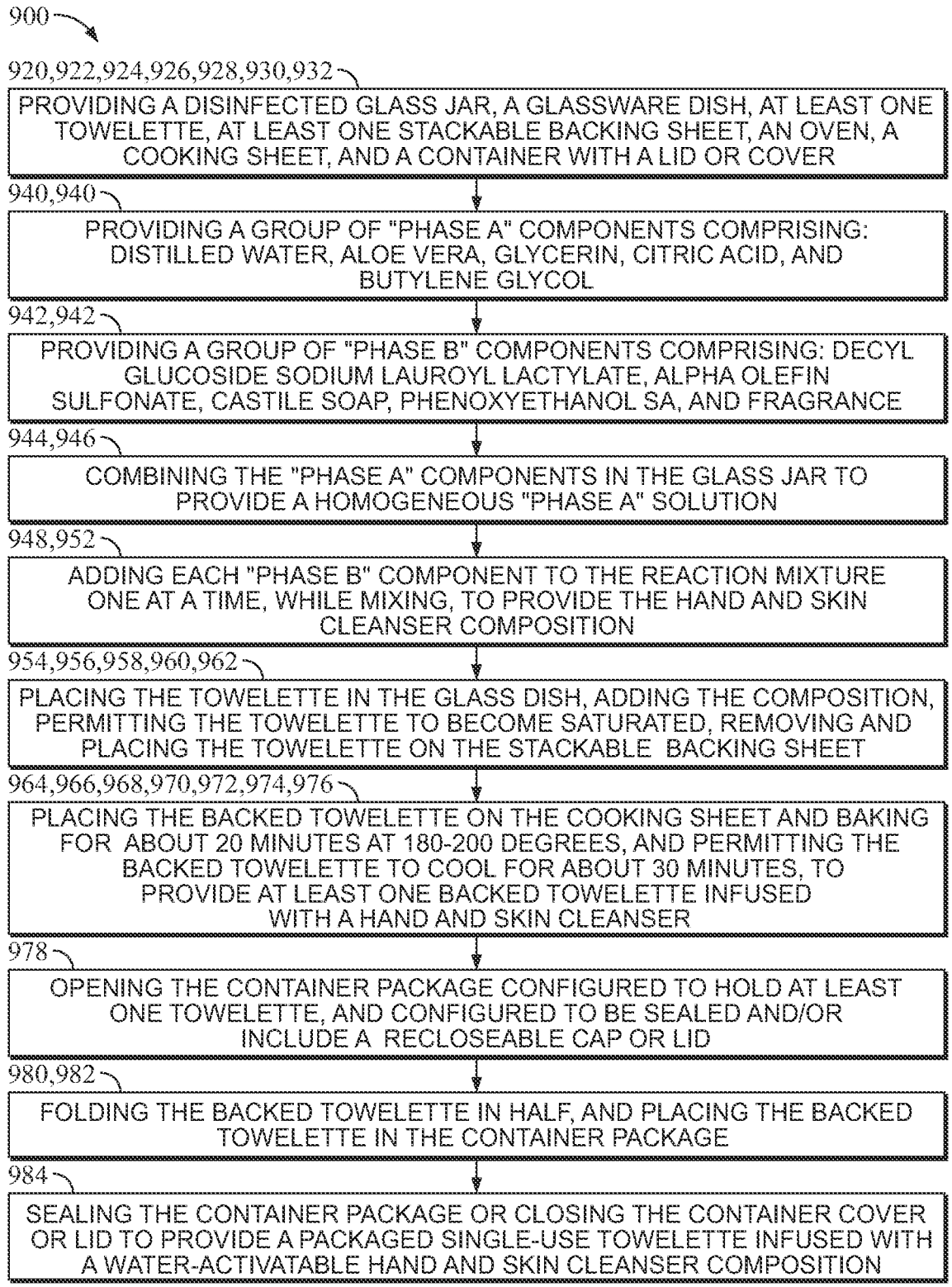
FIG. 9 presents a flow chart of a method in accordance with an exemplary embodiment of the present invention.

Referring now to FIG. 9, the present invention may provide a method 900 for manufacture of a single-use hand towelette infused with a water-activatable hand and skin cleanser, comprising one or more of the following steps and combinations thereof:
- 920 providing a disinfected laboratory glass jar;
- 922 providing a square or rectangular glassware dish;
- 924 providing at least one towelette of a nonwoven fabric;
- 926 providing at least one stackable backing sheet;
- 928 providing an oven;
- 930 providing an oven safe cooking sheet;
- 932 providing a container package configured to hold the at least one backed towelette, the container package comprising a container body and a recloseable container cover or lid;
- 940 providing a group of "phase A" components comprising:
- 940A a predetermined quantity of distilled water;
- 940B a predetermined quantity of aloe vera; 940C a predetermined quantity of glycerin;
- 940D a predetermined quantity of citric acid (pH 4.5); and
- 940E a predetermined quantity of butylene glycol;
- 942 providing a group of "phase B" components comprising:
- 942A a predetermined quantity of decyl glucoside sodium lauroyl lactylate blend;
- 942B a predetermined quantity of alpha olefin sulfonate;
- 942C a predetermined quantity of castile soap;
- 942D a predetermined quantity of phenoxyethanol SA; and
- 942E a predetermined quantity of fragrance;
- 944 adding the "phase A" components to the disinfected laboratory glass jar;
- 946 stirring the "phase A" components to provide a homogeneous "phase A" solution;
- 948 adding to a reaction mixture including the "phase A" solution, the "phase B" components, adding each of the "phase B" components to the reaction mixture one at a time, while mixing the reaction mixture under gentle agitation, to provide the hand and skin cleanser composition;
- 950 providing a pH testing device and testing the hand and skin cleanser composition for pH level, to confirm a pH of about 4.50;
- 952 providing a predetermined quantity of the hand and skin cleanser composition as described herein;
- 954 placing the at least one towelette in the glassware dish;
- 956 adding the predetermined quantity of the hand and skin cleanser composition to the glassware dish;
- 958 permitting the at least one towelette to become saturated with hand and skin cleanser composition in the glass-ware dish;
- 960 removing the at least one towelette from the glass-ware dish;
- 962 placing the at least one towelette on the at least one stackable backing sheet, to form a backed towelette;

964 placing the at least one backed towelette on the oven safe cooking sheet;

966 preheating the oven to a temperature of between about 180-200 degrees F.;

968 placing the cooking sheet with the at least one backed towelette thereon, into the preheated oven;

970 baking the at least one backed towelette for about 20 minutes;

972 removing the cooking sheet with the at least one backed towelette thereon, from the oven; 974 permitting the at least one backed towelette to cool for about 30 minutes;

976 providing the at least one backed towelette infused with a hand and skin cleanser;

978 opening the container package configured to hold the at least one backed towelette, the container package comprising a container body and a recloseable container cover or lid;

980 folding the at least one backed towelette in half;

982 placing the at least one backed towelette in the container body of the container package; and 984 sealing the container package or closing the container cover or lid, to provide at least one single-use towelette infused with a water-activatable hand and skin cleanser composition.

Figure 10:
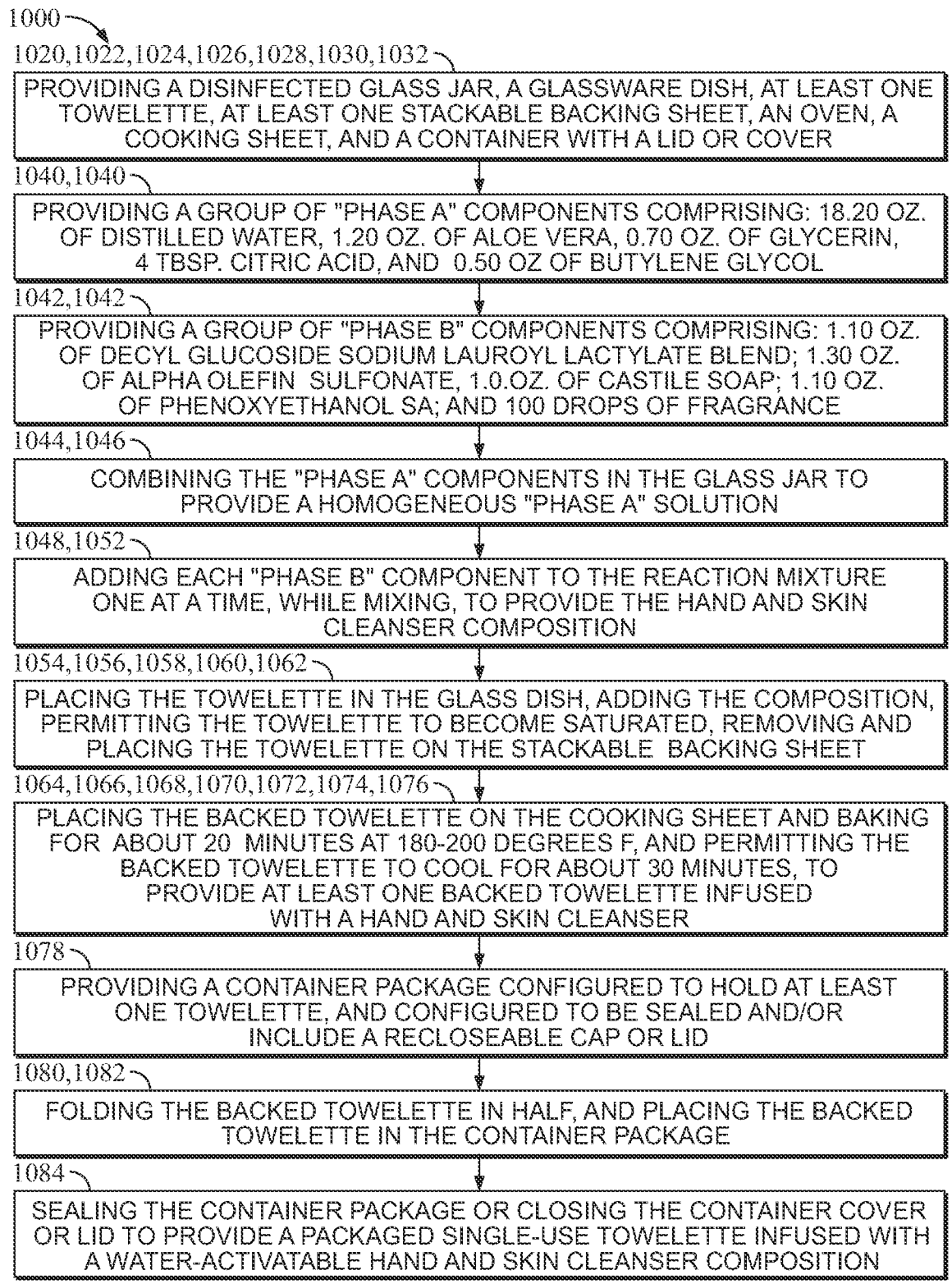
FIG. 10 presents a flow chart of a method in accordance with an exemplary embodiment of the present invention.

Referring now to FIG. 10, the present invention may provide a method 1000 for manufacture of a single-use hand towelette infused with a water-activatable hand and skin cleanser, comprising the following steps:

1020 providing a disinfected laboratory glass jar;

1022 providing a square or rectangular glassware dish;

1024 providing at least one towelette of a nonwoven fabric;

1026 providing at least one stackable backing sheet;

1028 providing an oven;

1030 providing an oven safe cooking sheet;

1032 providing a container package configured to hold the at least one backed towelette, the container package comprising a container body and a recloseable container cover or lid;

1040 providing a group of "phase A" components comprising:

1040A 18.2 oz. of distilled water;

1040B 1.20 oz. of aloe vera;

1040C 0.70 oz. of glycerin;

1040D 4 tbsp. of citric acid (pH 4.5); and 1040E 0.50 oz. of butylene glycol;

1042 providing a group of "phase B" components comprising:

1042A 1.10 oz. of decyl glucoside sodium lauroyl lactylate blend;

1042B 1.30 oz. of alpha olefin sulfonate;

1042C 1.0 oz. of castile soap;

1042D 1.10 oz. of a phenoxyethanol SA; and 1042E 100 drops of fragrance;

1044 adding the "phase A" components to the disinfected laboratory glass jar;

1046 stirring the "phase A" components to provide a homogeneous "phase A" solution;

1048 adding to a reaction mixture including the "phase A" solution, the "phase B" components, adding each of the "phase B" components to the reaction mixture one at a time, while mixing the reaction mixture under gentle agitation, to provide the hand and skin cleanser composition;

1050 providing a pH testing device and testing the hand and skin cleanser composition for pH level, to confirm a pH of about 4.50;

1052 providing a predetermined quantity of the hand and skin cleanser composition as described herein;

1054 placing the at least one towelette in the glassware dish;

1056 adding the predetermined quantity of the hand and skin cleanser composition to the glassware dish;

1058 permitting the at least one towelette to become saturated with hand and skin cleanser composition in the glass-ware dish;

1060 removing the at least one towelette from the glassware dish;

1062 placing the at least one towelette on the at least one stackable backing sheet, to form a backed towelette;

1064 placing the at least one backed towelette on the oven safe cooking sheet;

1066 preheating the oven to a temperature of between about 180-200 degrees F.;

1068 placing the cooking sheet with the at least one backed towelette thereon, into the preheated oven;

1070 baking the at least one backed towelette for about 20 minutes;

1072 removing the cooking sheet with the at least one backed towelette thereon, from the oven;

1074 permitting the at least one backed towelette to cool for about 30 minutes;

1076 providing the at least one backed towelette infused with a hand and skin cleanser;

1078 providing a container package configured to hold the at least one backed towelette, the container package comprising a container body and a recloseable container cover or lid;

1080 folding the at least one backed towelette in half, 1082 placing the at least one backed towelette in the container body of the container package; and 1084 sealing the container package or closing the container cover or lid, to provide at least one single-use towelette infused with a water-activatable hand and skin cleanser composition.

Figure 11:
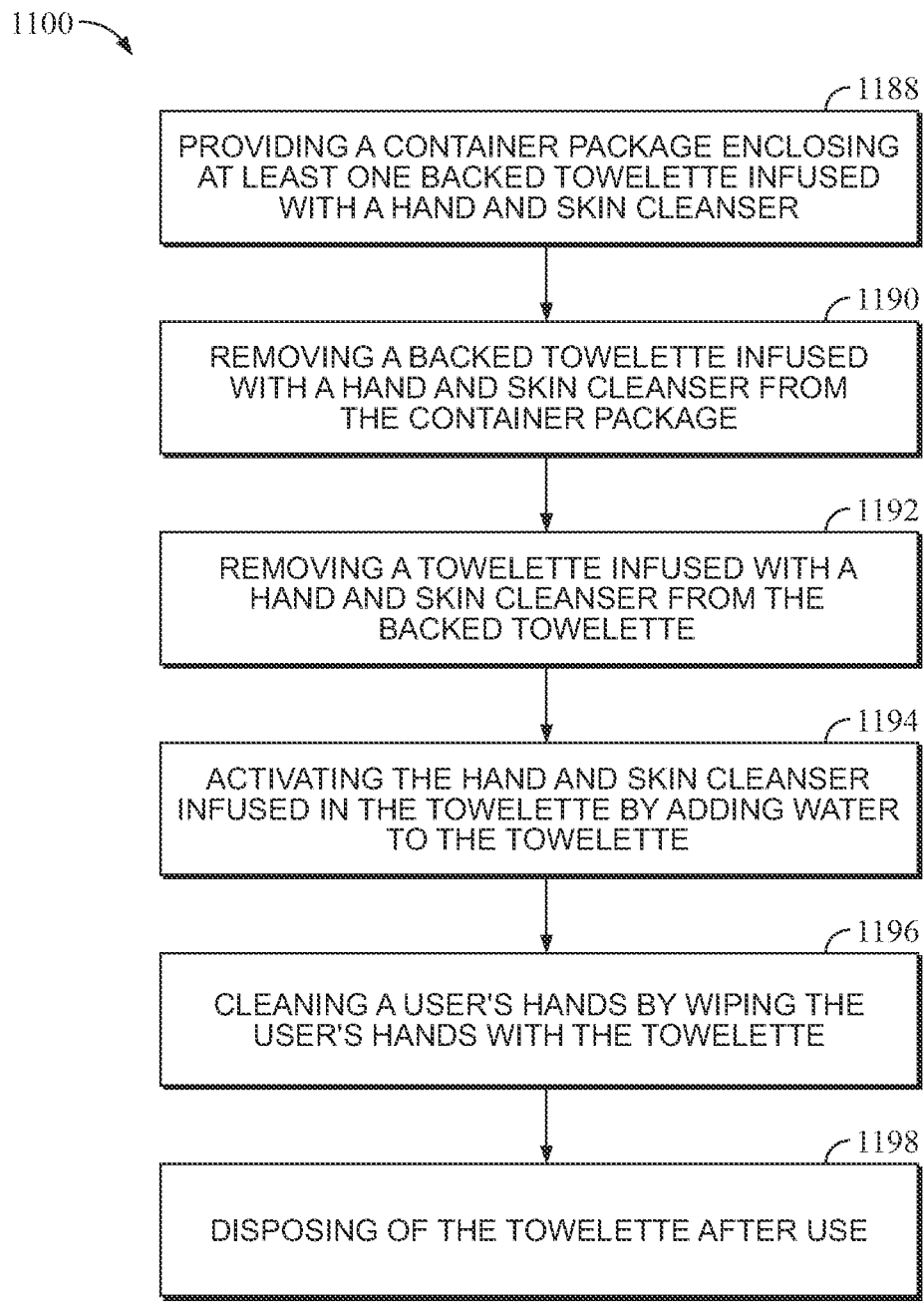
FIG. 11 presents a flow chart of a method in accordance with an exemplary embodiment of the present invention.

Referring now to FIG. 11, in an exemplary embodiment, the present invention provides a method 1100 for use of a towelette infused with a hand and skin cleanser, comprising the following steps:

1188 providing a container package enclosing at least one backed towelette infused with a hand and skin cleanser as described herein;

1190 removing a backed towelette infused with a hand and skin cleanser from the container package;

1192 removing a towelette infused with a hand and skin cleanser from the backed towelette;

1194 activating the hand and skin cleanser infused in the towelette by adding water to the towelette;

1196 cleaning a user's hands by wiping the user's hands with the towelette; and 1198 disposing the towelette after use.

In an exemplary embodiment, the present invention may provide a soap-infused, water-activated single-use hand towelette. The soap-infused water-activatable single-use hand towelette may be provided in a dry form. The towelette is capable of use as a dry towelette. In some embodiments, the towelette is provided in a dry state, and is moistened prior to use.

Figure 12:
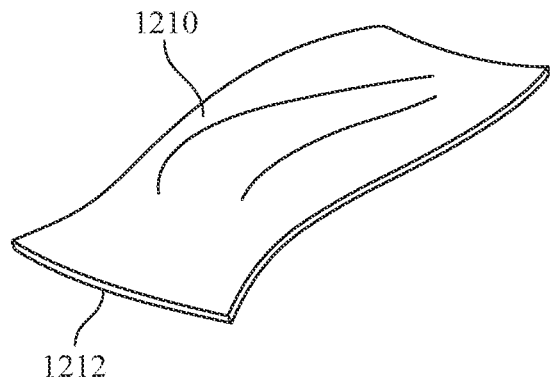
FIG. 12 presents a perspective view of a towelette in accordance with an exemplary embodiment of the present invention.

Referring to FIG. 12, a perspective view of a towelette 1210 is shown folded in half. The towelette may be made of any suitable material. In some embodiments, the towelette may be a cloth 1212 made of a nonwoven fabric. The towelette may be any suitable size or shape. In some embodiments, the towelette may be square, and may have dimensions comprising a length of up to about 7" and a width of up to about 7" wide.

Figure 13:
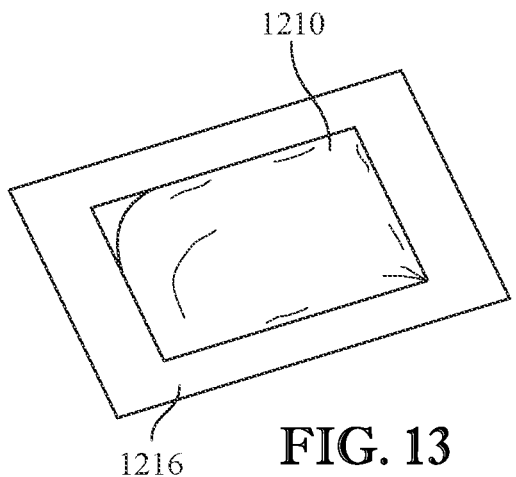
FIG. 13 presents a perspective view of a towelette on a backing in accordance with an exemplary embodiment of the present invention.

As shown in FIG. 13, a perspective view of a folded towelette 1210 on a backing 1216 in accordance with an exemplary embodiment of the present invention.

Figure 14:
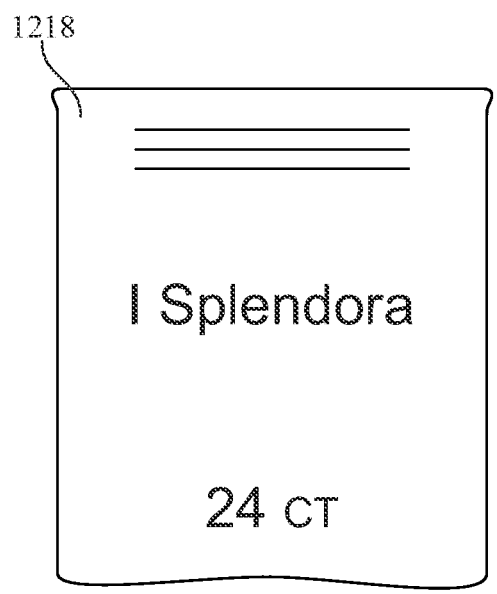
FIG. 14 presents a top view of a packaging container configured to enclose a plurality of towelettes in accordance with an exemplary embodiment of the present invention.

In some embodiments, the towelette 1210 may be individually wrapped. In some embodiments, a plurality of towelettes may be provided in a resealable packaging container. As shown at FIG. 14, a top view of a packaging container, the packaging container 1218 may be configured to enclose a plurality of towelettes. In some embodiments, the packaging container may enclose 24 towelettes. In some embodiments, the container package may enclose one backed towelette that is individually wrapped.

In summary, the present invention provides a water-activatable soap or hand and skin cleanser composition; a water-activated single-use hand towelette; and methods for manufacture, packaging, and use. The composition comprises distilled water, aloe vera, glycerin, citric acid, butylene glycol, decyl glucoside, a source of sodium lauroyl-, alpha olefin sulfonate, a paraben, and fragrance. The composition may be infused in a towelette comprising a nonwoven fabric.

The single-use hand towelette is provided in a dry state, and is moistened prior to use. The cleanser composition may be prepared by combining predetermined amounts of distilled water, aloe vera, glycerin, citric acid, and butylene glycol to provide a homogeneous "phase A" mixture; and adding and mixing, one by one, predetermined amounts of the remaining components to provide the hand and skin cleanser composition, which may have a pH of about 4.50. The towelette may be saturated with the composition, oven-dried, placed on a backing and packaged.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for manufacture of a packaged single-use hand towelette infused with a water-activatable hand and skin cleanser, comprising:
   providing a disinfected laboratory glass jar; providing a square or rectangular glassware dish;
   providing at least one towelette of a nonwoven fabric;
   providing at least one stackable backing sheet;
   providing an oven-safe cooking sheet;
   providing an oven;
   providing a group of "phase A" components comprising:
     a predetermined amount of distilled water,
     a predetermined amount of aloe vera; a predetermined amount of glycerin;
     a predetermined amount of citric acid having a pH 4.50; and
     a predetermined amount of butylene glycol;
   providing a group of "phase B" components comprising:
     a predetermined amount of decyl glucoside sodium lauroyl lactylate blend;
     a predetermined amount of alpha olefin sulfonate;
     a predetermined amount of castile soap;
     a predetermined amount of phenoxyethanol SA; and
     a predetermined amount of fragrance;
   adding the "phase A" components to the disinfected laboratory glass jar;
   stirring the "phase A" components to provide a homogeneous "phase A" solution;
   adding to a reaction mixture including the "phase A" solution, the "phase B" components, by adding each of the "phase B" components to the reaction mixture one at a time, while mixing the reaction mixture under gentle agitation, to provide the hand and skin cleanser composition;
   providing a pH testing device and testing the hand and skin cleanser composition for pH level, to confirm a pH of about 4.50;
   providing a predetermined quantity of the hand and skin cleanser composition; placing the at least one towelette in the glassware dish;
   adding the predetermined quantity of the hand and skin cleanser composition to the glassware dish;
   permitting the at least one towelette to become saturated with hand and skin cleanser composition in the glassware dish;
   removing the at least one towelette from the glassware dish;
   placing the at least one towelette on the at least one stackable backing sheet, to form at least one backed towelette;
   placing the at least one backed towelette on the oven-safe cooking sheet;
   preheating the oven to a temperature of between about 180 degrees F. to about 200 degrees F.; placing the cooking sheet with the at least one backed towelette thereon, into the preheated oven;
   baking the at least one backed towelette for about 20 minutes to dry the band and skin cleanser impregnated therein;
   removing the cooking sheet with the at least one backed towelette thereon from the oven;
   permitting the at least one backed towelette to cool for about 30 minutes;
   providing a container package configured to hold the at least one backed towelette, the container package comprising a container body and a recloseable container cover or lid;
   folding the at least one backed towelette in half;
   placing the at least one backed towelette in the container body of the container package; and
   sealing the container package, or closing the container cover or lid, thereby providing at least one packaged single-use hand towelette infused with a water-activatable hand and skin cleanser composition.

2. The method of claim 1 wherein providing a group of "phase A" components comprises providing a group of "phase A" components comprising:
   18.2 oz. of distilled water;
   1.20 oz. of aloe vera;
   0.70 oz. of glycerin;
   4 tbsp. of citric acid having a pH of 4.5; and
   0.50 oz. of butylene glycol.

3. The method of claim 2 wherein providing a group of "phase B" components comprises providing a group of "phase B" components comprising:
   1.10 oz. of decyl glucoside sodium lauroyl lactylate blend;
   1.30 oz. of alpha olefin sulfonate;
   1.0 oz. of castile soap;
   1.10 oz. of a phenoxyethanol SA; and
   100 drops of fragrance.

4. The method of claim 3 wherein the "group A" components and the "group B" components are provided in an equivalent proportion.

5. The method of claim 3 wherein the "group A" components and the "group B" components are provided in an equivalent proportion.

6. The method of claim 1 wherein the at least one towelette has a square shape, and has dimensions comprising a length of up to about 7" and a width of up to about 7".

7. A single-use hand towelette infused with a water-activatable hand and skin cleanser, comprising:
   a towelette of a nonwoven fabric on a backing sheet, the towelette being infused with a water activatable hand cleanser;
   wherein the water-activatable hand cleanser has a pH of about 4.50 and the water-activatable hand cleanser comprises:
      a predetermined amount of distilled water;
      a predetermined amount of aloe vera;
      a predetermined amount of glycerin;
      a predetermined amount of citric acid having a pH 4.50;
      a predetermined amount of butylene glycol;
      a predetermined amount of decyl glucoside sodium lauroyl lactylate blend;
      a predetermined amount of alpha olefin sulfonate;
      a predetermined amount of castile soap;
      a predetermined amount of phenoxyethanol SA; and
      a predetermined amount of fragrance.

8. The single-use hand towelette infused with a water-activatable hand and skin cleanser of claim 7, prepared by a method comprising:
   providing a disinfected laboratory glass jar; providing a square or rectangular glassware dish;
   providing a towelette of a nonwoven fabric;
   providing a stackable backing sheet;
   providing an oven-safe cooking sheet;
   providing an oven;
   providing a group of "phase A" components comprising:
      a predetermined amount of distilled water;
      a predetermined amount of aloe vera; a predetermined amount of glycerin;
      a predetermined amount of citric acid having a pH 4.50; and
      a predetermined amount of butylene glycol;
   providing a group of "phase B" components comprising:
      a predetermined amount of decyl glucoside sodium lauroyl lactylate blend;
      a predetermined amount of alpha olefin sulfonate;
      a predetermined amount of castile soap;
      a predetermined amount of phenoxyethanol SA; and
      a predetermined amount of fragrance;
   adding the "phase A" components to the disinfected laboratory glass jar;
   stirring the "phase A" components to provide a homogeneous "phase A" solution;
   adding to a reaction mixture including the "phase A" solution, the "phase B" components, by adding each of the "phase B" components to the reaction mixture one at a time, while mixing the reaction mixture under gentle agitation, to provide the hand and skin cleanser composition;
   providing a pH testing device and testing the hand and skin cleanser composition for pH level, to confirm a pH of about 4.50;
   providing a predetermined quantity of the hand and skin cleanser composition;
   placing the towelette in the glassware dish;
   adding the predetermined quantity of the hand and skin cleanser composition to the glassware dish;
   permitting the towelette to become saturated with hand and skin cleanser composition in the glassware dish;
   removing the towelette from the glassware dish;
   placing the towelette on the at least one stackable backing sheet, to form a backed towelette;
   placing the backed towelette on the oven-safe cooking sheet;
   preheating the oven to a temperature of between about 180 degrees F. to about 200 degrees F.;
   placing the cooking sheet with the backed towelette thereon, into the preheated oven;
   baking the backed towelette for about 20 minutes to dry the hand and skin cleanser impregnated therein;
   removing the cooking sheet with the backed towelette thereon from the oven; permitting the backed towelette to cool for about 30 minutes;
   whereby the single-use hand towelette infused with a water-activatable hand and skin cleanser is ready for use.

9. The method of claim 8 wherein providing a group of "phase A" components comprises providing a group of "phase A" components comprising:
   18.2 oz. of distilled water;
   1.20 oz. of aloe vera;
   0.70 oz. of glycerin;
   4 tbsp. of citric acid having a pH of 4.5; and
   0.50 oz. of butylene glycol.

10. The method of claim 9 wherein providing a group of "phase B" components comprises providing a group of "phase B" components comprising:
   1.10 oz. of decyl glucoside sodium lauroyl lactylate blend;
   1.30 oz. of alpha olefin sulfonate;
   1.0 oz. of castile soap;
   1.10 oz. of a phenoxyethanol SA; and
   100 drops of fragrance.

11. The method of claim 10 wherein the "group A" components and the "group B" components are provided in an equivalent proportion.

12. The method of claim 10 wherein the "group A" components and the "group B" components are provided in an equivalent proportion.

13. The method of claim 7 wherein the towelette has a square shape, and has dimensions comprising a length of up to about 7" and a width of up to about 7".

14. A package of single-use hand towelettes infused with a water-activatable hand and skin cleanser, comprising:
   a resealable container package; and
   a plurality of backed single-use hand towelettes infused with a water-activatable hand and skin cleanser;
   wherein the plurality of backed single-use hand towelettes are prepared by a method comprising:
      providing a disinfected laboratory glass jar;
      providing a square or rectangular glassware dish;
      providing a plurality of towelettes of a nonwoven fabric;
      providing a plurality of stackable backing sheets;
      providing at least one oven-safe cooking sheet;
      providing an oven;
      providing a group of "phase A" components comprising:
         a predetermined amount of distilled water;
         a predetermined amount of aloe vera;
         a predetermined amount of glycerin;

a predetermined amount of citric acid having a pH 4.50; and
a predetermined amount of butylene glycol;
providing a group of "phase B" components comprising:
a predetermined amount of decyl glucoside sodium lauroyl lactylate blend;
a predetermined amount of alpha olefin sulfonate;
a predetermined amount of castile soap;
a predetermined amount of phenoxyethanol SA; and
a predetermined amount of fragrance;
adding the "phase A" components to the disinfected laboratory glass jar;
stirring the "phase A" components to provide a homogeneous "phase A" solution;
adding to a reaction mixture including the "phase A" solution, the "phase B" components, by adding each of the "phase B" components to the reaction mixture one at a time, while mixing the reaction mixture under gentle agitation, to provide the hand and skin cleanser composition;
providing a pH testing device and testing the hand and skin cleanser composition for pH level, to confirm a pH of about 4.50;
providing a predetermined quantity of the hand and skin cleanser composition;
placing the plurality of towelettes in the glassware dish;
adding the predetermined quantity of the hand and skin cleanser composition to the glassware dish;
permitting the plurality of towelettes to become saturated with hand and skin cleanser composition in the glassware dish;
removing the plurality of towelettes from the glassware dish;
placing each towelette of said plurality of towelettes one stackable backing sheet of said plurality of stackable backing sheets, to form a plurality of backed towelettes;
placing the plurality of backed towelettes on the at least one oven-safe cooking sheet;
preheating the oven to a temperature of between about 180 degrees F. to about 200 degrees F.;
placing the at least one cooking sheet with the plurality of backed towelettes thereon, into the preheated oven;
baking the backed towelettes for about 20 minutes to dry the hand and skin cleanser impregnated therein;
removing the at least one cooking sheet with the plurality of backed towelettes thereon from the oven; and
permitting the plurality of backed towelettes to cool for about 30 minutes to provide a plurality of single-use band towelettes infused with a water-activatable hand and skin cleanser;

providing a container package configured to hold the plurality of single-use hand towelettes, the container package comprising a container body and a recloseable container cover or lid;
folding each single-use hand towelette of said plurality of single-use hand towelettes in half;
placing the plurality of single-use hand towelettes in the container body of the container package; and
sealing the container package, or closing the container cover or lid, thereby providing a plurality of packaged single-use hand towelettes infused with a water-activatable hand and skin cleanser composition.

15. The method of claim 14 wherein providing a group of "phase A" components comprises providing a group of "phase A" components comprising:
18.2 oz. of distilled water;
1.20 oz. of aloe vera;
0.70 oz. of glycerin;
4 tbsp. of citric acid having a pH of 4.5; and
0.50 oz. of butylene glycol.

16. The method of claim 15 wherein providing a group of "phase B" components comprises providing a group of "phase B" components comprising:
1.10 oz. of decyl glucoside sodium lauroyl lactylate blend;
1.30 oz. of alpha olefin sulfonate;
1.0 oz. of castile soap;
1.10 oz. of a phenoxyethanol SA; and
100 drops of fragrance.

17. The method of claim 16 wherein the "group A" components and the "group B" components are provided in an equivalent proportion.

18. The method of claim 16 wherein the "group A" components and the "group B" components are provided in an equivalent proportion.

19. The method of claim 16 wherein the container package is configured to enclose a plurality of individually wrapped towelettes.

20. The method of claim 19 wherein the plurality of individually wrapped towelettes comprises 24 individually wrapped towelettes.

21. The method of claim 16 wherein the container package is configured to enclose a plurality of backed towelettes that are stacked therein.

22. The method of claim 21 wherein the plurality of backed towelettes comprises 24 backed towelettes.

23. The method of claim 14 wherein each towelette of said plurality of towelettes has a square shape, and has dimensions comprising a length of up to about 7" and a width of up to about 7".

* * * * *